US008119162B2

(12) United States Patent
Miksa et al.

(10) Patent No.: US 8,119,162 B2
(45) Date of Patent: Feb. 21, 2012

(54) PARTICLES THAT DISRUPT OR IMPEDE BACTERIAL ADHESION, RELATED COMPOSITIONS AND METHODS

(75) Inventors: Davide Miksa, Newark, DE (US); Harsh M. Trivedi, Somerset, NJ (US); Tao Xu, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 412 days.

(21) Appl. No.: 11/271,306

(22) Filed: Nov. 10, 2005

(65) Prior Publication Data

US 2007/0104660 A1    May 10, 2007

(51) Int. Cl.
*A61K 9/14*     (2006.01)
*A61K 8/00*     (2006.01)

(52) U.S. Cl. .......................................... 424/489; 424/49
(58) Field of Classification Search .................. None
See application file for complete search history.

(56) References Cited

U.S. PATENT DOCUMENTS

| | | | |
|---|---|---|---|
| 4,138,477 A | | 2/1979 | Gaffar |
| 4,770,183 A * | | 9/1988 | Groman et al. .............. 424/9.32 |
| 5,547,682 A | | 8/1996 | Chagnon et al. |
| 2002/0028455 A1 | | 3/2002 | Laibinis et al. |
| 2005/0064027 A1 | | 3/2005 | Jacob et al. |
| 2006/0121123 A9 * | | 6/2006 | Boppart et al. .............. 424/491 |

FOREIGN PATENT DOCUMENTS

| | | |
|---|---|---|
| CA | 1063357 | 10/1979 |
| CA | 2431004 | 12/2001 |
| EP | 0625 353 A1 | 11/1994 |
| EP | 0 737 470 A2 | 10/1996 |
| JP | S60-001564 A | 1/1985 |
| JP | H03-183642 A | 8/1991 |
| JP | H05-502944 A | 5/1993 |
| JP | 6-239722 A | 8/1994 |
| JP | H08-500700 A | 1/1996 |
| JP | 9-175923 A | 7/1997 |
| JP | H09-002926 A | 7/1998 |
| JP | H10-182382 A | 7/1998 |
| RU | 2234337 | 8/2004 |
| WO | WO 02/074275 | 9/2002 |
| WO | WO 2005/030141 | 4/2005 |
| WO | WO 2006080895 A1 * | 8/2006 |

OTHER PUBLICATIONS

Fong et al, Organophilic Colloidal Particles with a Synthetic Polypeptide Coating, Langmuir, 1999, 15, 4421-4426.*
Hughes, G. & Nevell, T.P., "The Mechanism of the Oxidation of Glucose by Periodate". *Tran. Farad. Soc.*, 1948, vol. 44, pp. 941-948.
Elender, G.; Kuhner, M.; Sackmann, E., *Biosensors & Bioelectronics.* 1996, vol. 11, pp. 565-577.
Beyer, D. et al. "Covalently attached polymer mono- and multilayers on silanized glass substrates", *Thin Solid Films* 284-285, 1996, pp. 825-828.

(Continued)

*Primary Examiner* — Michael G Hartley
*Assistant Examiner* — Paul Dickinson
(74) *Attorney, Agent, or Firm* — Nikhil A. Heble

(57) ABSTRACT

Oral care and other compositions comprising particles having cores attached to bioadhesive polymers for inhibition of pellicle formation, plaque formation, biofilm formation, biofouling, and microbial adhesion or attachment are described. Methods using said compositions to treat surfaces, such as oral surfaces.

18 Claims, 3 Drawing Sheets

OTHER PUBLICATIONS

Kuhner, M. & Sackmann, E., "Ultrathin Hydrated Dextran Flims Grafted on Glass: Preparation and Characterization of Structural, Viscous, and Elastic Properties by Quantitatve Microinterferometry", *Langmuir*, 1996, vol. 12, pp. 4866-4876.

Dai et al., "Biomedical coatings by the covalent immobilization of polysaccharides onto gas-plasma-activated polymer surfaces", *Surface and interface Analysis*, 2000, vol. 29, pp. 46-55.

Mason et al., "Attachment of hyaluronic acid to polypropylene, polystyrene, and polytetrafluoroethylene", *Biomaterials*, 2002, vol. 21, pp. 31-36.

Hartley, P.G., "Physicochemical Properties of Polysaccharide Coatings Based on Grafted Multilayer Assemblies", *Langmuir*, 2002, vol. 18, pp. 2483-2494.

Grasset, F. et al., "Surface modification of zinc oxide nanoparticles by aminopropyltriethoxysilane", *Journal of Alloys and Compounds*, 2003, vol. 360, pp. 298-311.

Hardman, J.G. et al., *Goodman & Gilman's The Pharmacological Basis of Therapeutics*, 10th Edition, 2001.

Allen Jr., L.V., *The Art, Science, and Technology of Pharmaceutical Compounding*, 2nd Edition, 2003.

Rowe, R.C. et al., *Handbook of Pharmaceutical Excipients*, 4th Edition, 2003.

International Search Report and Written Opinion in International Application No. PCT/US06/060785 mailed Apr. 16, 2007.

\* cited by examiner

PARTICLES THAT DISRUPT OR IMPEDE BACTERIAL ADHESION, RELATED COMPOSITIONS AND METHODS

BACKGROUND OF THE INVENTION

The process of tooth decay has been the subject of intense scrutiny. Tooth decay is typically caused by a process that begins with formation of plaque, which contains acid-secreting bacteria that etch and erode the tooth surface and otherwise irritate or attack the gingival and soft dental tissue surfaces. Plaque formation begins minutes after tooth brushing or professional tooth cleaning, with bacterial attachment taking place within a few hours thereafter.

Regular, repeated plaque removal is the main route by which tooth decay is kept in abeyance, although professionally-applied, solid polymeric sealants have been utilized as replaceable protective coatings to prevent direct contact of plaque bacteria and their acids with the tooth surface. Antibacterial agents have also been included in dental treatment compositions both to kill oral bacteria and, in some cases, to provide a temporary residual effect against bacterial propagation in the plaque layer formed after toothbrushing with the composition.

However, it would be desirable to provide an efficient strategy to prevent or inhibit bacterial attachment to tooth and oral soft tissue surfaces, without the need to seal the tooth in a contiguous polymer layer, and without the need to involve intervention of a dental professional.

BRIEF SUMMARY OF THE INVENTION

The invention provides particles that disrupt and/or impede the attachment of bacteria to an oral surface and compositions containing the particle. The particle includes (i) a core that has an oxide compound or salt and (ii) a bioadhesive polymer. The bioadhesive polymer is attached to the oxide compound or salt. Also provided are processes for preparing the particle, methods for inhibiting or reducing the formation of plaque on an oral surface using the particle, and other related methods.

DETAILED DESCRIPTION OF THE DRAWINGS

Figure 3:
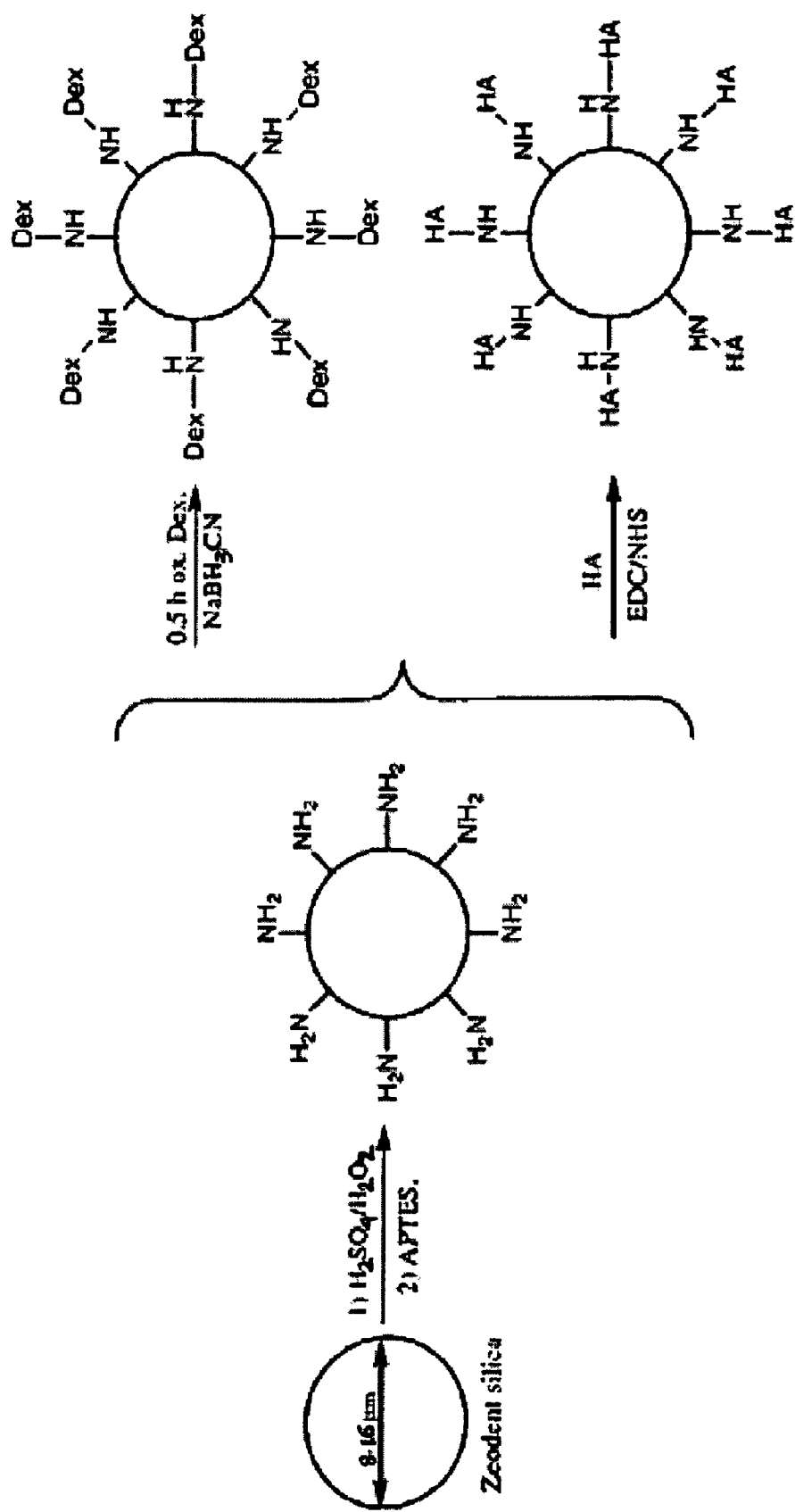

FIG. 3 provide a graphic representation of the overall process for preparing a particle according to an embodiment of the present invention by pre-treating the particle core (e.g., silica) with a compound that provides tethered amino groups attached to the surface thereof, followed by reaction chemistry to link a carbonyl or acid group-containing polymer to the tethered amino groups.

DETAILED DESCRIPTION OF THE INVENTION

The present invention relates to compositions and methods for inhibiting biofilm formation and bacterial adhesion to surfaces, including industrial, household, medical, human and animal somatic surfaces, particularly oral plaque deposition and bacterial adhesion to dental surfaces.

The compositions described herein prevent and/or disrupt bacterial attachment to teeth, gums and other oral surfaces, without requiring application of a contiguous polymer layer.

The present invention also provides an approach to deliver benefit for prevention of bacterial adhesion/attachment to biological and other surfaces generally (e.g., tooth surfaces, mucosal surfaces, and/or derma surfaces). The approach takes advantage of the anti-fouling properties of bioadhesive polymers, preferably polysaccharides and related polymers, such as polysaccharides, dextran, and hyaluronate (HA). Particles according to the present invention are provided that comprise such polymers stably attached to solid particle cores, such as particle cores of silicon oxide ($SiO_2$) or zinc oxide (ZnO). These particles are applied to surfaces, which may be biological surfaces, such as oral surfaces, in order to create a barrier against microbial (e.g., bacterial) attachment thereto, as well as against attachment to the treated surface by organic molecules (e.g., organic scum components). The present invention provides methods for inhibiting bacterial attachment to such surfaces, e.g., the tooth and oral soft tissue surfaces, thereby inhibiting the onset and/or rate of biofilm formation and deposition and/or reducing the strength of biofilm adhesion, which in the case of oral use can thereby inhibit the onset of dental caries and periodontal diseases such as gingivitis and periodontitis. The particles, e.g., of $SiO_2$ or ZnO, can be, and preferably are, included in formulations for application to a surface, for example, dentifrice formulations and other oral care consumer products, and may also be included in oral care products for the dental professional.

Particles according to the present invention include a core. The particle core(s) may be a solid particle core(s) that is at least substantially water insoluble. In one embodiment, the particle cores will be particulate entities comprising one or more of the at least substantially water insoluble, metals, semi-metals, and non-metals; metal, semi-metal, non-metal, and mixed-metal halides, carbides, nitrides, sulfides, oxides (including, e.g., carbonates, phosphates, sulfates), and the like, as well as ceramics, minerals (including biominerals), and alloys thereof. Examples of such substances include: AgBr, AlN, $Al_2O_3$, $BaLiF_3$, $BaY_2F_8$, $Bi_2O_3$, CdS, CdSe, CdTe, CuCl, FeC, $Fe_4N$, $Fe_2O_3$, GaAs, GaP, HgS, HgSe, HgTe, InAs, InP, InSn, KI, $LiCaAlF_6$, LiNb, NaCl, NiO, SiC, $Si_3N_4$, $SiO_2$, $SnO_2$, TiN, $TiO_2$, $WO_3$, $YLiF_4$, ZnC, ZnS, ZnSe, ZnTe, ZrN, ZnO, Sn, Ag, Au, Cu, Ni, Pt, carbon, silicon, germanium; compounds, salts, and complexes comprising them; and mixtures of any of the foregoing with one another or with a further component.

In one embodiment, a metal(s) for use in such metal compounds, salts, and mixtures will be chosen from alkali metals, alkaline earth metals, Zn, Sn, Fe, Se, Cu, Mn, Mo, Co, Ni, Cr, V, W, Ti, and Al, preferably from alkali metals, alkaline earth metals, Zn, Sn, Fe, Cu, Mn, Mo, and Ti, more preferably from alkali metals, alkaline earth metals, and Zn. In one preferred embodiment, the metal(s) will comprise any one of alkaline earth metals, Zn, or a combination thereof with one another or with an alkali metal(s) or both.

In one embodiment, the solid particle cores will comprise an oxide compound or its salt. Preferred oxides include substantially water insoluble: simple oxides, carbon oxides (e.g., metal carbonates), phosphorus oxides (e.g., metal phosphates, metal polyphosphates), sulfur oxides (e.g., metal sulfates), silicates, and combinations thereof. In one embodiment, the particle core will comprise a simple oxide compound. Examples of simple oxide compounds include $Al_2O_3$, $Fe_2O_3$, $MgAl_2O_4$, $SiO_2$, $SnO_2$, $TiO_2$, and ZnO, and combinations thereof, e.g., $xMOy$-$zAl_2O_3$—$SiO_2$ systems (M being a metal cation(s)). In a preferred embodiment, the simple oxide compound may be $SiO_2$ or ZnO.

In one embodiment, the particle core will comprise at least one oxide compound or salt that is a carbon oxide, phosphorus oxide, sulfur oxide, or silicate. Preferred examples for each of these respectively include homo- and hetero-metal: 1) carbonates, e.g., $CaCO_3$, $CaMg(CO_3)_2$; 2a) polyphosphates such as pyrophosphates, e.g., $Ca_2P_2O_7$, $CaMgP_2O_7$, and 2b) phosphates, e.g., $Ca_3(PO_4)_2$, hydroxyapatites such as $Ca_{10}(PO_4)_6(OH)_2$), oxyapatites such as $Ca_{10}(PO_4)_6O$, haloapatites, haloahydroxyapatites, and halo-oxyapatites such as $Ca_{15}(PO_4)_9(F)O$; 3) sulfates, e.g., $CaSO_4$ and sulfate apatites such as $Na_6Ca_4(SO_4)_6(F,Cl)_2$; and 4) silicates, e.g., $Al_2SiO_5$, sodium silicates, calcium silicates, and micas. In one embodiment, metal carbonates, phosphates, and sulfates are preferred. Combination oxides belonging to more than one such class may be used, e.g., carbonate apatites such as $Ca_{10}(PO_4)_6CO_3$, silicate sulfate apatites such as $Ca_{10}(SiO_4)_3(SO_4)_3(OH,F,Cl)_2$, carbonate sulfates such as $Ca_2(SO_4)(CO_3)$, phosphate sulfates such as $Ca_2HPO_4SO_4$, and silicate phosphates and sulfate phosphates such as the calcium silicate phosphates or sulfate phosphates, e.g., $Ca_5(SiO_4,PO_4,SO_4)_3(F,Cl,O,OH)$.

The solid particle cores may alternatively or in addition comprise polymer(s) that are at least substantially water insoluble, and preferably not significantly water-swellable, such as polyolefins, polystyrenes, polycarbonates, polyesters (including polyhydroxyalkanoates), and the like. Where a particle core is selected for use in an oral care composition, it will be orally acceptable, e.g., no significant toxicity under the conditions and concentrations used, etc.

The particle cores are preferably substantially water insoluble. As used herein, this means that the particle cores will retain their dimensions under aqueous conditions at a pH between pH6 and pH8, for at least 3 hours, preferably for at least 4, at least 5, or at least 6 hours. In some cases, the particles, deposited on the oral surface, may come into contact with bacterial or food acids. Where such acidic conditions are to be present, preferably the material for the particle core will be one that is either resistant to such acid attack, or will be one that erodes or degrades to produce non-toxic products. Examples of particle core materials that can degrade under acidic conditions to produce non-toxic products include the non-toxic metal carbonates, sulfates, and phosphates, preferably where the metal comprises a non-toxic alkaline earth metal, preferably calcium (i.e., Ca(II) cation).

The use of such acid-degradable materials for particle cores in an oral composition can provide a population of particles layered upon oral surfaces, which particles remain insoluble until bacterial accumulation has occurred to the point that microbial acid production is significant. From that point, such a layer of particles behaves as a sacrificial, acid-neutralizing layer that provides further protection to the tooth against acid attack. Such particles can also provide a benefit by helping neutralize acids from other sources, as well, such as food acids (e.g., saturated and unsaturated carboxylic acids, including acetic, oxalic, citric, malic, and tartaric acids; and phosphoric acid) and gastric acids, which are similarly capable of eroding dental enamel.

The particle cores may have any morphology. Preferred morphologies include those that are at least substantially: spheroidal, ellipsoidal, or flat. The particle cores may have any size, preferably less than 1 mm. In one embodiment, the average maximum dimension of the particle cores, i.e. their average largest diameter or other axial dimension, will preferably be from about 1 nm to about 100 μm, more preferably from about 10 nm to about 100 μm. Thus, in one embodiment, the core sizes will be nanoscopic or microsopic in scale. In one embodiment, the particle cores will have an average size of about 1 to about 100 μm, preferably about 5 to about 50 μm, more preferably about 5 to about 25 μm. In one embodiment, the particle core sizes will be from about 1 nm to about 1 μm; thus, the particle core can have the dimensions of a colloid. In one embodiment, the particle core can have the dimensions of a single molecule. Thus, the overall particle can have the form of a regular or irregular hyperbranched structure, e.g., a dendrimer or brush architecture. Such molecular-scale cores are distinguished from larger-scale "super-molecular" scale particles used as cores, e.g., those of 1 nm to 1 mm size.

Super-molecular-scale particle cores may be porous or non-porous; in one embodiment, they will be at least substantially non-porous. Where a porous material is used in or as the particle core, the pores thereof may optionally contain an orally acceptable, e.g.: medicament, such as an antibacterial agent (e.g., triclosan), an antioxidant, or a pain relief agent; a nutraceutical, such as a botanical extract (e.g., magnolia extract, tea extract); vitamin; breath freshening agent; or other agent or combination thereof to be released in the oral cavity.

The attachments may be and means known in the art, and may include any type of bond attachment form and/or one or more intervening or linker molecule(s). The particles will comprise the particle core conjugated to at least one bioadhesive polymer that has been attached to the particle by covalent or non-covalent binding. In the case of covalent binding to the core, this will take place by reaction involving reactive group pairs: one member of the pair being provided by the particle core, or a linker or other reactive group pre-attached thereto, and one member by the polymer, or a linker or other reactive group pre-attached thereto. In one embodiment, the reactive group provided by the polymer will be a primary or secondary carbonyl group(s) or acid group(s).

Bioadhesive polymers include any natural or synthetic homo- or hetero-polymer that is capable of adhering, whether by physical attraction or chemical reaction, to a desired target surface, e.g., a hard or soft oral surface, throughout the minimum time considered effective for the selected use. Preferred examples of classes of bioadhesive polymers include:

(1) polysaccharides and related polymers;
(2) polypeptides (including dipeptides, oligopeptides), such as albumins, caseins, collagens, fibrins, gelatins, globulins (e.g., immunoglobulins), lectins, prolamins (such as avenins, gliadins, glutelins, glutens, glutenins, hordeins, kafirins, oryzins, pennisetins, secalins, zeins), synthetic polyamides, and targeted polypeptides (e.g., polypeptide aptamers);
(3) acrylic polymers, such as homo- and hetero-polymers of acrylate and/or acrylamide monomers, including acrylate and (e.g., $C_1$-$C_4$) alkylacrylate salts and esters, and (e.g., $C_1$-$C_4$) alkylacrylamides, with one another (e.g., polymethylmethacrylates) and/or with alginic acid or other comonomers, cyanoacrylates;
(4) other poly-acid polymers, such as homo- and heteropolymers of non-acrylic, unsaturated carboxylic acids, e.g., other poly(unsaturated carboxylic, i.e. mono-, di-, and poly-carboxylic, acid) polymers, such as poly(crotonic, itaconic, and/or maleic acid) polymers, polyphosphates, poly(organic-phosphate or -phosphonate) polymers, poly(organic-sulfate or -sulfonate) polymers, poly(unsaturated hydroxycarboxylic acid) polymers, and the like;
(5) polyesters, including homo- and hetero-polyhydroxyalkanoates (e.g., polylactic acid polymers, polyglycolides, and the like), functionalized polyesters (e.g., carboxylated polyesters, hydroxypolyesters), and polyorthoesters;
(6) polyanhydrides, such as poly(fumaric-co-sebacic) acid polymers;
(7) polyalkylene polymers, such as synthetic polyalkylenes, polyalkylene glycols (e.g., polyethylene glycols), polyalkylene oxides, polyalkylene terephthalates, and the like;
(8) polysiloxanes;
(9) polyurethanes; and
(10) polyvinyl polymers, such as poly(vinyl alcohols), polyvinyl esters, polyvinyl ethers, polyvinyl halides, polyvinylphenols, and polyvinylpyrrolidones.

Such bioadhesive polymers may be provided in the form of linear or branched polymers, or may be provided in the form of larger structures comprising such polymers, e.g., colloids or latexes. In some cases, a monomer of such a bioadhesive polymer may itself provide bioadhesion. Thus, in some embodiments, the bioadhesive can be a bioadhesive monomer, such as an amino acid or a monosaccharide.

Bioadhesive polymers can be readily obtained from commercial sources including, e.g., Fluka (Ronkonkoma, N.Y., USA), Polysciences (Warrenton, Pa., USA), and Sigma-Aldrich (Milwaukee, Wis., USA; and St. Louis, Mo., USA); or can be synthesized from monomers obtained from these suppliers using well-known techniques.

In one embodiment, the bioadhesive polymer will be a biocompatible polymer. In one embodiment, the polymer will be a polysaccharide or related polymer. Examples of useful polysaccharides and related polymers include: poly(saccharides); poly(mono- and di-deoxy saccharides); poly(sugar acids), e.g., poly(glyc-uronic, -onic, -aric, and -ulosonic acids); poly(sugar alcohols); and poly(amino sugars).

Such polysaccharides and related polymers may be based on any aldose or ketose monomers, such as: aldo- or keto-triose, tetroses, pentoses, hexoses, heptoses; their deoxy, acid, alcohol, and amine cognates; their substituted derivatives; and the like. Thus, polysaccharide and related polymers useful herein may comprise substituted or unsubstituted monomer unit(s), or both. Where substituted monomer unit(s) are present in the polysaccharide or related polymer, the substitutions will preferably be selected from $C_1$-$C_4$: alkyl ether (e.g. methyl, ethyl, or propyl ether), hydroxyalkyl ether, and carboxyalkyl ether substitutions; alkylamine and alkanoylamine (e.g., N-acetyl), or sulfamidic, sulfonamidic, and sulfamic (e.g., N-sulfo), substitutions; alkanoyl ester, e.g., pyruvic, acetic, and formic ester, or sulfoxy or phosphoxy acid ester, substitutions (on polymer hydroxyl groups); and alkanol, diol, and polyol ester substitutions (on polymer acid groups).

In one embodiment, the monomeric units of the polysaccharide or related polymer will preferably be selected from the substituted and unsubstituted hexose, hexulose, hexonic acid, hexuronic acid, hexaric acid, hexulosonic acid, pentose, pentulose, pentonic acid, penturonic acid, pentonic acid, and pentulosonic acid residues. In one embodiment, the polymer will be a glucose, glucose acid, and/or glucose alcohol polymer or copolymer.

Representative examples of preferred polysaccharides and related polymers include: celluloses; chitosans; starches; glycogens; gums, e.g., plant, microbial, and algal gums, such as agaroses, guars, dextrans, and carrageenans, and synthetic polysaccharide-based gums; and glycosaminoglycans, e.g., dermatans, chondroitins, heparans, hyaluronates, and keratins, including dermatan sulfate, chondroitin sulfate, heparan sulfate, heparin, and keratan sulfate; substituted saccharide polymers, e.g., alkyl celluloses, hydroxyalkyl celluloses, carboxyalkyl celluloses, cellulose esters (including, e.g., nitrocelluloses), and the like; microbial exopolymers; and structures comprising such polymers, e.g., marine colloids and synthetic hydrocolloids of polysaccharides. In one preferred embodiment, the polysaccharide or related polymer will be a poly or copoly(saccharide), a gum, or a glycosaminoglycan; preferred gums include dextran; preferred glycosaminoglycans include hyaluronic acid.

In one embodiment, the bioadhesive polymer will be a polycarboxylate polymer, for example, any one of the: poly(acrylate and/or methacrylate) polymers; other poly(acid) polymers; and carboxylated derivatives of any polymer class, such as a carboxylated polysaccharide or related polymer, carboxylated polypeptide (e.g., a poly(acidic-side-chain) peptide), or a carboxylated polyester. Examples of carboxylated polysaccharides and related polymers include alginates, carboxymethylated polysaccharides (e.g., carboxymethyl starch, carboxymethyl cellulose), hyaluronates, oxidized polysaccharides (e.g., oxidized starch, oxidized guar gum), pectates, polyaspartate, polyglutamates, xanthans, and the like.

Polymers to be attached to the core can be chemically modified to increase bioadhesion. For example, the polymers can be modified by altering the number of negatively charged (e.g., carboxylate) groups and/or positively charged (e.g., amino) groups, present on the polymer surface. Such modifications can be made in order to enhance the ability of the polymer to adhere to charged surface domains of dental tissues. For example, bare regions of dental enamel may present a number of positively charged surface domains, while salivary glycoprotein-coated zones on enamel often present negatively charged domains. Polymers respectively having negative or positive charges, i.e. under the conditions of use, may be selected, prepared, or modified, so as to obtain an advantageous degree of polymer adhesion to such surface charges. Chemical modifications to the polymers may be made by employing any of the useful linkage chemistries known in the art, such as those described in U.S. Patent Application Publication No. 2005/064027 A1 to Jacob et al., the contents of which are incorporated herein by reference.

In one embodiment, the bioadhesive polymer will be a hydrophilic bioadhesive polymer. In one embodiment, the hydrophilic bioadhesive polymer will be any that provide an adhesive effect when deposited on or attached to a surface in an aqueous environment; preferably it will be a hydrophilic polymer that is capable of forming hydrogels (including, e.g., true gels, microgels, quasi-gels, pseudo-gels, and the like) or hydrocolloids.

Useful bioadhesive polymers for attachment to a particle core will be those that are capable of physically or chemically adhering to the particle core such that, under conditions of use, the polymer will not separate from the core for about 3 hours or more, and preferably until, e.g., the core degrades or the polymer is chemically or biologically hydrolyzed by components of the environment.

In one embodiment, the bioadhesive polymer will be covalently linked to the core. In one embodiment, the bioadhesive polymer will be covalently linked to a moiety that is a linker, which is itself covalently or non-covalently linked to the core. Such a linker may be first attached to the core and then contacted with the bioadhesive polymer, or may first be attached to the bioadhesive polymer, and then contacted with the core. All three components may be concurrently attached together. Alternatively, a first linker may be attached to the core, and a second linker may separately be attached to the polymer, the first and second linkers jointly providing a reactive group pair that can be covalently linked, or jointly providing non-covalently-interacting surfaces that form a stable non-covalent attachment; followed by contacting the derivatized cores and derivatized polymers. Alternatively, the particle core may be covalently attached to a linker that is capable of forming stable non-covalent attachment to the bioadhesive polymer.

In embodiments in which the bioadhesive polymer is covalently attached to either a linker or directly to the core surface, the polymer will have at least one reactive group that is useful for reacting to provide a covalent linkage, e.g., any one of: a carbonyl group, such as an aldehyde group; an amine group, such as a primary amine group, an acid group or derivative, such as an amide or ester, e.g., a carboxylic acid, amide, or ester; a hydroxide group; and the like. In one embodiment, a preferred bioadhesive polymer will be one that contains, or that has been derivatized to contain, an aldehyde or carboxylic acid group(s).

As is the case for any biopolymers lacking a desired reactive group, where a bioadhesive polymer is selected that does not have any carbonyl or acid groups, or any aldehyde or carboxylic acid groups in particular (if desired), or does not have a number or carbonyl or acid groups sufficient for the practitioner's desire, then the polymer will be pre-treated to provide such group(s) before reaction to link the polymer to the particle core or to the linker. Likewise, where other linking chemistries are chosen, the reactive groups may be already present in the polymer and particle core, or may be added thereto by pretreatment.

Thus, other linkage chemistries may alternatively be employed, wherein the polymer and the particle core or linker together provide a reactive group pair, one of the two providing a nucleophilic group, and the other provide an electrophilic group. The nucleophile and the electrophile groups may be already present on the particle core or linker, or the polymer, or the particle core or linker and/or the polymer may be pretreated to contain them, using any of the many chemistries known useful in the art therefor. Representative examples of such chemistries include those employing nucleophile and the electrophile group pairs such as those listed in Table 1.

TABLE 1

Exemplary Reactive Group Pairs For Attachment Chemistries

| Nucleophile | Electrophile | Attachment |
|---|---|---|
| Amine | Alkyl carbodiimide-activated ester | Amide |
| | Bromoacetamide | Amine |
| | Carboxyl | Amide |
| | Chloroacetamide | Amine |
| | Cyclic carboxylic anhydride | Amide |
| | 9-Fluorenylmethoxycarbonyl | Amide |
| | N-Hydroxysuccinimide ester | Amide |
| | Isocyanate | Urea |
| | Isothiocyanate | Thiourea |
| | Phosphate | Phosphoramide |
| | Phosphonate | Phosphonamide |
| | Sulfonate | Sulfonamide |
| Alcohol (or Thiol) | Alkyl carbodiimide-activated ester | Ester (or Thioester) |
| | Bromoacetamide | Ether (or Thioether) |
| | Carboxyl | Ester (or Thioester) |
| | Chloroacetamide | Ether (or Thioether) |
| | Cyclic carboxylic anhydride | Ester (or Thioester) |

TABLE 1-continued

Exemplary Reactive Group Pairs For Attachment Chemistries

| Nucleophile | Electrophile | Attachment |
|---|---|---|
| | Ester | Ester (or Thioester) |
| | 9-Fluorenylmethoxycarbonyl | Ester (or Thioester) |
| | N-Hydroxysuccinimide ester | Ester (or Thioester) |
| | Maleimido | Ester (or Thioester) |
| | Semicarbazido | Ester (or Thioester) |
| | Thiosemicarbazido | Ester (or Thioester) |
| | Alkyl tosylate, mesylate, brosylate, nosylate, nonaflate, triflate, or tresylate salts | Ether (or Thioether) |

In one preferred embodiment, the reactive group pair will comprise an amine group provided by the particle core and a polymer aldehyde group with which it forms a Schiff base that is then reduced (e.g., using a cyanoborohydrate salt) to form a secondary amine linkage. In one preferred embodiment, the reactive group pair will comprise an amine group provided by the particle core and a polymer acid group that has been derivatized in a process using carbodiimide chemistry to form a succinimide ester.

The set of bioadhesive polymer molecules conjugated to the particle core(s) may comprise more than one type of polymer, and/or more than one type of attachment to the particle core. For example, a particle core may comprise tethers of different lengths to which the polymer(s) are to be attached, or different electrophilic or nucleophilic groups may be provided on the particle core surface or on the distal end of the linker, so that a variety of different reaction chemistries are used to attach the polymer(s) thereto.

In an embodiment in which the particle core provides an amino group for the linking reaction, this will preferably be a tethered primary or secondary amino group, preferably a tethered primary amino group that has been added to the surface of the particle core by pre-treatment with an amino group-containing agent. Preferred amino group-containing agents for this purpose include, e.g., amino silicone compounds.

In one preferred embodiment, an amino silicone compound will be an (omega-aminoaliphatyl)-tri(aliphatoxy)siloxane of the formula

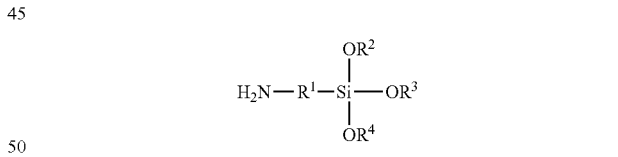

wherein $R^1$ is a $C_1$-$C_8$ homo- or hetero-hydrocarbon group, and $R^2$, $R^3$, and $R^4$ are independently selected from $C_1$-$C_8$ homo- or hetero-hydrocarbon groups, hydrocarbon in either case referring to cyclic, alicyclic, branched, and linear hydrocarbons. As used herein, the term $C_1$ homo- or hetero-hydrocarbon group refers to organic groups containing one carbon atom, examples of which include —$CH_3$—, —$CH_2$—, —$CH_2SiH_2$—.

In one embodiment thereof, $R^1$ will be selected from the $C_1$-$C_8$ aliphatic (including cycloaliphatic) groups. In one embodiment, $R^2$, $R^3$, and $R^4$ will be independently selected from the $C_1$-$C_8$ alphatic groups.

In one embodiment thereof, $R^1$ will be selected from the $C_1$-$C_5$ alkyl groups. In one embodiment, $R^2$, $R^3$, and $R^4$ will be independently selected from the $C_1$-$C_5$ alkyl groups. In one embodiment, the selected $R^1$ group will be larger than any of the selected groups for $R^2$, $R^3$, and $R^4$. In one embodiment, $R^2$ and $R^4$ will be identical groups. In one embodiment, $R^2$, $R^3$, and $R^4$ will be identical groups. In one embodiment, $R^1$ will be a $C_1$, $C_2$, $C_3$, or $C_4$ group; preferably a n-propa-1,3-diyl group. In one embodiment, $R^2$, $R^3$, and $R^4$ will independently be ethyl or methyl; preferably $R^2$, $R^3$, and $R^4$ will all be ethyl or will all be methyl.

Preferred examples of useful (omega-aminoalkyl)-trialkoxysiloxanes include: 3-aminopropyltriethoxysilane, $H_2N(CH_2)_3Si(OCH_2CH_3)_3$; 3-aminopropyltrimethoxysilane, $H_2N(CH_2)_3Si(OCH_3)_3$; 2-aminoethyltrimethoxysilane, $H_2N(CH_2)_2Si(OCH_3)_3$; and 2-aminoethyltriethoxysilane, $H_2N(CH_2)_2Si(OCH_2CH_3)_3$.

Reaction conditions useful for particle pretreatments and for linkage reactions are well known in the art. Any such conditions may be used, such as those described in the examples below.

The particles hereof may be provided for use in the form of a composition comprising them. A composition according to the present invention may comprise a mixture of different particles that vary from one another in the identity of the core material, porosity, size, morphology, polymer identity, or polymer-to-particle attachment.

A composition hereof may be a dentifrice (e.g., paste, gel, powder, or liquid dentifrice), prophylaxis paste, dental paint, lozenge, chewing gum, or other abrasive, detergent, or cleansing composition capable, either alone or in combination with the action of an applicator, of removing deposits, such as plaque, from teeth and/or from oral soft tissues. Similar solid, semi-solid, and liquid formats may be useful for other topical and for systemic uses, e.g., as well as tablets, capsules, ointments, creams, pre-gels, lavages, surgical site washes, parenteral solutions and suspension, and suppositories. Compositions may also be formulated as industrial or consumer product paints, sprays, cleansers, dips, rinses, and the like.

Alternatively, a topical or oral composition may be designed as a post-cleansing treatment composition, such as a liquid-gel, slurry, or suspension mouthwash or mouth rinse. In oral, topical, and systemic somatic uses, the composition will respectively comprise orally, topically, or systemically acceptable substances. Such substances include a solid, semisolid, or liquid carrier, and may optionally include one or more: other active ingredients, e.g., antibacterial agents (e.g., a water-insoluble non-cationic antibacterial agent, such as triclosan), antioxidants, pharmaceuticals, vitamins, fluoride sources, nutraceuticals, and the like; excipients and inert ingredients, e.g., humectants, gelling agents, thickeners, solvents, diluents, binders, fillers, plasticizers, anti-caking agents, disintegrants, gums, emollients, oleochemicals, colorants, flavorants, odorants, pH adjusting agents (acids, bases), buffers, surfactants, emulsifiers, suspending agents, enzymes, coatings (e.g., enteric, acrylic, or carbohydrate or cellulosic coatings), chelants, preservatives, and the like. Representative examples of such well-known additives are described, e.g., in copending U.S. Patent Application Ser. Nos. 60/639,080 to Worrell et al. for Dentifrice Comprising Green Tea Extract (filed Dec. 23, 2004); 60/639,331 to Xu et al. for Oral Care Compositions Containing Flavonoids and Flavans (filed Dec. 22, 2004); and 60/639,169 to Boyd et al. for Oral Compositions Containing Oolong Tea Extract (filed Dec. 23, 2004); as well as in L. V. Allen Jr., *The Art, Science, and Technology of Pharmaceutical Compounding* (2d ed., 2003); J. G. Hardman et al., *Goodman & Gilman's The Pharmacological Basis of Therapeutics* ($10^{th}$ ed., 2001); and R. C. Rowe et al., *Handbook of Pharmaceutical Excipients* ($4^{th}$ ed., 2003); all of which are hereby incorporated by reference in their entirety.

A composition according to the present invention comprises a carrier. Carriers are commonly water, aqueous humectant, and/or aqueous alcohol mixtures of a consistency appropriate for the selected mode of administration of the composition, e.g., as a paste, gel, tablet, lozenge, syrup, rinse, and so forth. Carriers for oral compositions according to the present invention include all known in the art.

Such orally acceptable carriers include the usual components of toothpastes, tooth powders, prophylaxis pastes, mouth rinses, lozenges, gums and the like, and are more fully described hereinafter. Selection of specific carrier components is dependant on the desired product form, including dentifrices, rinses, gels, and confectionaries.

In various embodiments, the orally acceptable dentifrice carrier used to prepare an oral composition comprises a water-phase. As recognized by one of skill in the art, the oral compositions of the present invention optionally include other materials, such as for example, viscosity modifiers, diluents, surface active agents, such as surfactants, emulsifiers, and foam modulators, pH modifying agents, abrasives, humectants, emollients, and moisturizers, mouth feel agents, sweetening agents, flavor agents, colorants, preservatives and combinations thereof. It is understood that while general attributes of each of the above categories of materials may differ, there may be some common attributes and any given material may serve multiple purposes within two or more of such categories of materials. Preferably, such carrier materials are selected for compatibility with the particles, as well as with other ingredients of the composition.

In the case of mouth washes, sprays, or rinses, orally acceptable carriers typically comprise an aqueous phase comprising water or a water and alcohol mixture. Further, in various embodiments, the oral carrier comprises a humectant and/or a surfactant. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70 to about 99.9% of the preparation. In various embodiments, the alcohol is typically ethanol or isopropanol. The pH of such liquid and other preparations of the invention is generally in the range of from about 4.5 to about 10, which can be achieved and/or maintained with a pH control agent (acid or base) and/or a buffer such as sodium citrate, benzoate, carbonate, or bicarbonate, disodium hydrogen phosphate, or sodium dihydrogen phosphate.

In the case of, e.g., lozenges, tablets, and beads, an orally acceptable carrier can be a non-cariogenic, solid water-soluble polyhydric alcohol (polyol) such as mannitol, xylitol, sorbitol, malitol, hydrogenated starch hydrozylate, hydrogenated glucose, hydrogenated disaccharides or hydrogenated polysaccharides, in an amount of about 85 to about 95% of the total composition. Emulsifiers such as glycerin, and tableting lubricants, in minor amounts of about 0.1 to 5%, may be incorporated into the tablet, bead or lozenge formulation to facilitate the preparation of the tablet beads and lozenges. In the case of dentifrices including toothpowders, toothpastes (dental creams), and gels, an orally acceptable carrier may comprise water and humectant typically in an amount ranging from about 10% to about 80% of the oral composition.

In one embodiment, a composition, as formulated for application in the selected end-use, according to the present invention will comprise an amount of particles that is about 50% or less by weight of the composition, or about or less than 40%, 30%, 20%, or 10% of the composition. In one embodiment, the composition will comprise from about 1% to about 10% by weight of the composition, more preferably about 5%. Compositions hereof may also be provided as concentrated pre-mixes, or the pure particles may be supplied in frozen, dry, or lyophilized form, with instructions for the manner of using these to prepare a final formulation for use. In such compositions, the composition can comprise more than 50%, and up to 100% of the weight thereof.

Particles according to the present invention are useful for efficiently delivering bioadhesive polymers to the oral surfaces, where they adhere to block attachment or adhesion by bacteria. Preferably, an orally acceptable composition comprising the particles is applied to the oral cavity by contacting oral surface(s) with the composition. In an embodiment, particles introduced into the oral cavity, either during or after cleansing of oral surfaces, can remain resident upon cleansed oral surfaces to inhibit or reduce bacterial attachment, plaque formation, and the like. Compositions hereof may also be used to prevent or reduce bacterial adhesion to skin, hair, medical implants, stents, IV lines, implements, and the like.

Compositions hereof may also be used to prevent or reduce biofilm formation or microbial adhesion in contexts other than oral, topical, systemic, or even somatic applications. For example, biofilm formation, microbial adhesion, and biofouling may be reduced in marine and freshwater applications, or in aqueous handling (storage or transport) or treatment systems, by applying such a composition to surfaces of that are in, or are to be placed into, contact with an aqueous environment. Such compositions can also be used as biofilm release enhancers, such as for use on re-usable components of such marine, freshwater, and aqueous handling or treatments systems, e.g., mesh screens, filter plates, filtering cartridges, and the like.

Such compositions may be applied to industrial or to household system components to inhibit biofilm formation and/or to provide a biofilm release agent to facilitate removal of, e.g., mildew, algae, fungi, bacteria, and organic scum during cleaning. For example, the compositions may be advantageously applied to, e.g., boats, ships, rafts, flotation platforms, pontoon bridges, docks, food processing surfaces, grout, sinks, faucets, water fountains and fonts, birdbaths, swimming pools and accessories (e.g., stairs, slides), air humidifiers, drain holes and pipes, storage tanks, water pump and stirring vanes, drain plugs and strainers, condensation drip pans, toilet bowls, toilet reservoirs, bathtub mats and other bathtub accessories (shelf units, footpads, shower curtains), bathtub and pool covers, sliding door tracks, bathtub and shower enclosures, aquarium surfaces, animal watering bottles and bowls, and the like.

Thus, in one method according to the present invention, a composition comprising the inventive particles will be applied to a surface upon which deposition of the particles is desired. The non-deposited ingredients of the composition may then remain in contact with the surface, but are more often rinsed away or bioabsorbed. In one preferred embodiment, the composition will be a cleansing composition (e.g., an abrasive and/or detergent composition) formulated for cleaning of the surface, e.g., a wash. In one embodiment, the composition will be any capable of depositing the particles on a new or already-cleaned surface, e.g., a rinse.

In a method according to the present invention, inventive particles are prepared by process comprising providing a core, a bioadhesive polymer, and optionally a linker, and attaching the bioadhesive polymer to the core.

EXAMPLES

Example 1

Pretreatment of Particles to Add Tethered Amine Groups $SiO_2$ (ZEODENT® silica, 8-16 μm average diameter particles, available from J.M Huber Corp., Edison, N.J., USA) are etched clean with a strongly oxidizing solution of $H_2SO_4$/$H_2O_2$ (75%/25% v/v). Next, the $SiO_2$ is modified by deposition of 3-aminopropyltriethoxysilane (APTES). Although solution deposition is preferred, vapor deposition may be substituted therefor. The vapor deposition route utilizes strict anhydrous conditions, as may be afforded, e.g., by a dry glove box, in order to avoid unwanted hydrolysis reactions. Solution deposition under acidic conditions provides a more widely applicable procedure. In this approach $SiO_2$ is dispersed in distilled $H_2O$ and the pH of the resulting solution is adjusted to an approximate pH value of 6.5 with $HNO_3$. The suspension is then stirred for 1 hour, after which time 1 mL of APTES is added, and the suspension stirred again. After 24 hours of stirring, the excess APTES is removed by filtration and washing with ethanol and acetone. Cross-linking of the deposited APTES molecules is desirable. In order to promote the cross-linking (i.e. condensation) of individual APTES molecules on the $SiO_2$ surface, the modified silica is dried at 800° C., preferably for about 8 hours. ZnO particles may be similarly pre-treated to provide pendant amine groups.

Example 2

Preparation of Particles Conjugated to Polysaccharide Gum

Figure 1:
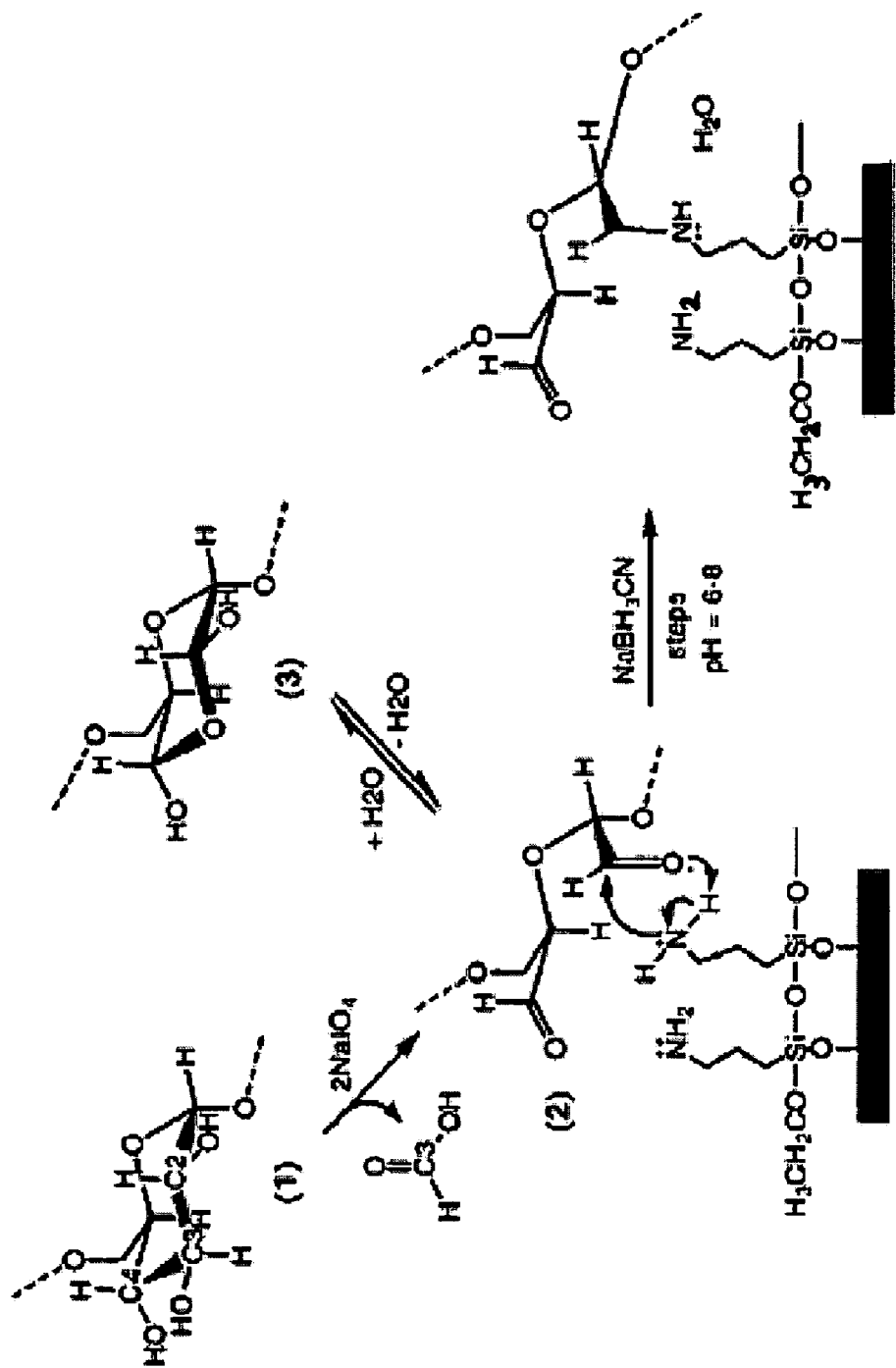
FIG. 1 illustrates a reaction scheme for oxidation of a polysaccharide to provide carbonyl groups, followed by reacting the resulting polymer to attach it to the surface of a solid particle core, by reaction of the carbonyl groups with amine groups.

The microbial gum, dextran, is covalently attached to amino-modified particle cores prepared according to Example 1, i.e. APTES-modified $SiO_2$ particles (hereinafter $SiO_2$+APTES). The polysaccharide is first pre-treated to provide carbonyl groups thereon. As shown in FIG. 1, the dextran is treated with sodium periodate ($NaIO_4$) to oxidize the saccharide ring(s), forming aldehyde carbonyl groups and releasing formic acid. The product of the oxidation reaction is the dialdehyde corresponding to (2). The surface bound APTES is able to reductively aminate (2) to form a Schiff base (structure not shown), which is reduced by sodium cyanoborohydrate ($NaBH_3CN$) to form a stable secondary amine linkage. Since the extent of dextran oxidation controls the amount of (2) produced, it also controls the grafting density (i.e. number of bonds) between dextran and the $SiO_2$+APTES. In order to optimize the dextran grafting density, a variety of dextran oxidation times are employed, e.g.: 0.5, 1, 2, 4, and 24 hours. Other experimental parameters that are considered are the size (i.e. molecular weight) and polydispersity (i.e. broadness of molecular weight distribution) of dextran. These two structural properties will also affect the extent of interaction between individual $SiO_2$ particles. The result is dextran-linked $SiO_2$ particles.

Example 3

Preparation of Particles Conjugated to Glycosaminoglycan

Figure 2:
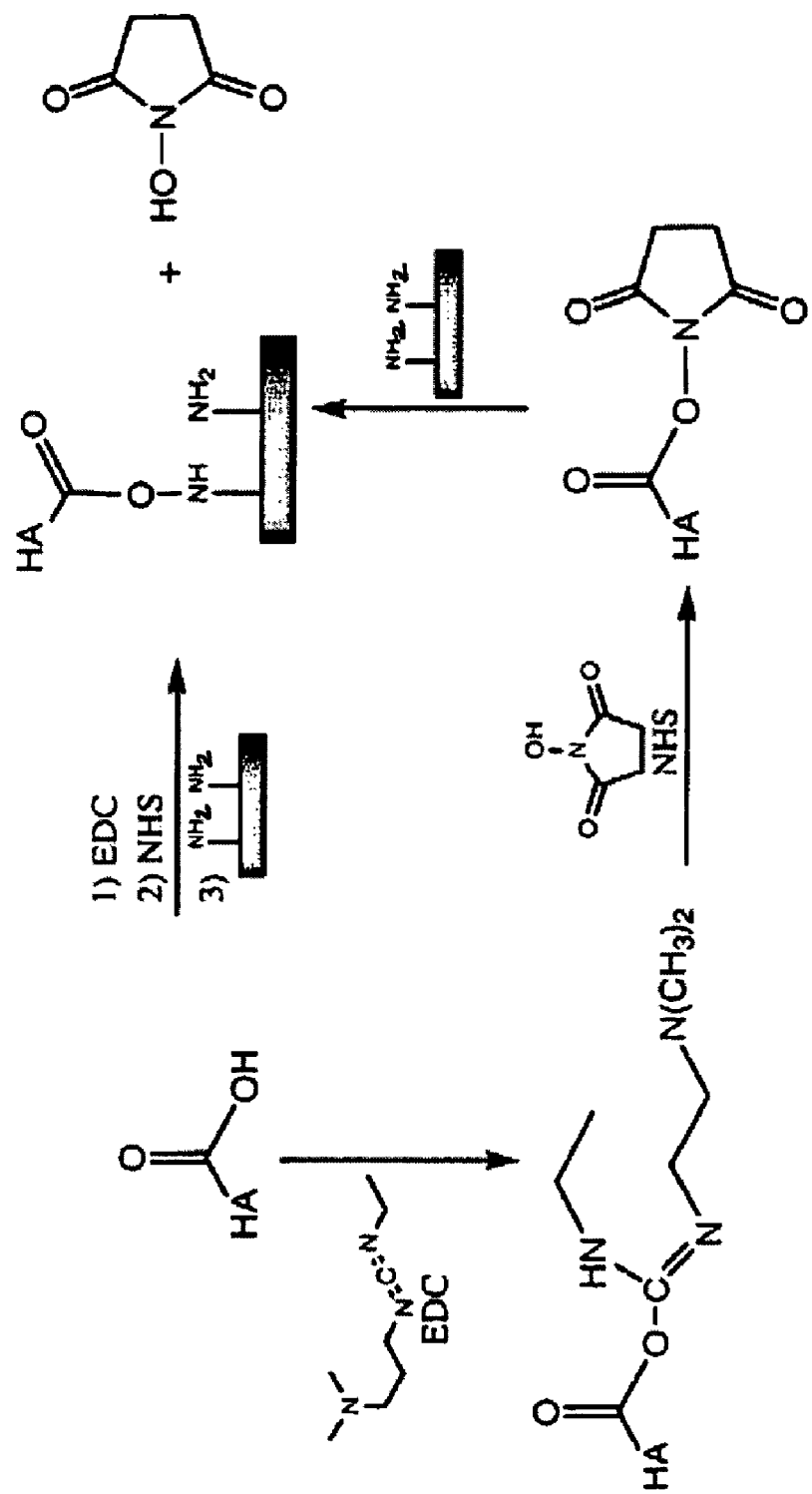
FIG. 2 illustrates a reaction scheme for attaching a carboxylic acid-containing polymer to the surface of a solid particle core, by reaction of a carboxyl hydroxy group, using carbodiimide chemistry and N-hydroxysuccinimide, to form a succinimide ester, which is then reacted with amino groups tethered to the particle core surface to form an amino alkanoate (i.e. alkanoyloxy-amino) linkage.

Hyaluronate (HA) is covalently grafted to hereinafter $SiO_2$+APTES particles, prepared as in Example 1. Since HA has a carboxylate functionality, no modification is necessary prior to grafting. Covalent attachment of hyaluronate to $SiO_2$+APTES is achieved by N-ethyl-N'-(3-dimethylaminopropyl)carbodiimide(EDC)/N-hydroxysuccinimide (NHS) coupling chemistry (see FIG. 2). The grafting density of hyaluronate on $SiO_2$+APTES is controlled by varying the EDC/NHS ratio.

Note that, for HA, periodate chemistry, such as described in Example 2, can alternatively be used to form aldehyde carbonyl groups to produce an HA derivative that can be covalently attached to a particle core by reaction involving such carbonyl groups. Similarly, polymers having primary amine groups, hydroxyl groups, or acid (or ester or amide) groups can be covalently attached to a raw or derivatized particle core by reaction involving any one or more of those chemical groups present in the polymer with a corresponding reactive pair group present on the particle core.

The overall modification process is shown schematically in FIG. 3, which illustrates the preparation of $SiO_2$+APTES particles conjugated to a dextran derivative, as described in Example 2, or with HA residues as described in Example 3.

Preferred concentrations of the particles in an orally acceptable composition can be determined by routine analysis of a series of test compositions containing, e.g. different concentrations of particles of any given size(s) or size range(s), to which the polymer(s) have been conjugated, e.g., under a series of conditions, such as the extent of pre-treatment of the polymer or the particle core or the time provided for the conjugation reaction. The rate or degree of inhibition of bacterial attachment to a mouth, or to an oral cavity model (such as an "artificial mouth"), treated with the compositions can be assessed by quantitative or semi-quantitative analysis, such as by a calorimetric technique to assess bacterial accumulation or pellicle formation on hydroxyapatite disks.

We claim:

1. An oral composition comprising:
   a particle comprising:
   a core comprising an oxide compound or its salt and
   a bioadhesive polymer surrounding the core,
   wherein the bioadhesive polymer is attached to the outer surface of the core by a linker, wherein the linker comprises an amino silicone moiety;
   and an orally acceptable carrier,
   wherein the composition is in the form of a dentifrice, lozenge, or confectionary.

2. The oral composition according to claim 1, wherein the bioadhesive polymer is selected from a polysaccharide, a polypeptide, a polyanhydride polymer, or a polycarboxylate polymer.

3. The oral composition according to claim 1, wherein the bioadhesive polymer is selected from a polysaccharide and a polycarboxylate polymer.

4. The oral composition according to claim 1, wherein the bioadhesive polymer is selected from a substituted or unsubstituted poly(saccharide) polymer, poly(deoxysaccharide) polymer; poly(sugar acid) polymer, poly(sugar alcohol) polymer, an acrylic or other poly-acid polymer, and a carboxyalkylpolysaccharide.

5. The oral composition according to claim 1, wherein the bioadhesive polymer is selected from a cellulose, a chitosan, a starch, a glycogen, a substituted saccharide polymer, and a microbial exudate,
   wherein a substituted monomer of the substituted saccharide polymer is selected from
   alkyl ether, hydroxyalkyl ether, and carboxylalkvl ether,
   alkylamine, alkanoylamine, sulfamidic, sulfonamidic, sulfamic, and alkanoyl esters, and alkanol, diol, and polyol ester substitutions.

6. The oral composition according to claim 1, wherein the bioadhesive polymer is selected from a polysaccharide gum and a glycosaminoglycan.

7. The oral composition according to claim 1, wherein the bioadhesive polymer is selected from a dextran and a hyaluronate.

8. The oral composition according to claim 1, wherein the oxide compound or salt of the core is selected from a metal oxide, a nonmetal oxide, a semi-metal oxide and a salt thereof.

9. The oral composition according to claim 8, wherein the oxide or salt is selected from a metal carbon oxide, a metal phosphorus oxide, a metal sulfur oxide, and a metal silicate.

10. The oral composition according to claim 8 wherein the oxide compound is selected from $SiO_2$ and $ZnO$.

11. The oral composition according to claim 9, wherein the oxide compound is selected from an alkaline earth metal carbonate, an alkaline earth metal phosphate, and an alkaline earth metal sulfate.

12. The oral composition according to claim 1, wherein the linker is at least one omega-aminoaliphatyl-tri(aliphatoxy) silane molecule.

13. The oral composition according to claim 12, wherein the omega-aminoaliphatyl-tri(aliphatoxy) silane molecule is selected from 3-aminopropyltriethoxysilane, 3-aminopropyltrimethoxysilane, 2-aminoethyltrimethoxysilane, and 2-aminoethyltriethoxysilane.

14. A method for inhibiting or reducing the formation of plaque on an oral surface comprising contacting the oral surface with a particle according to claim 1.

15. A method for inhibiting or reducing the attachment of bacteria on an oral surface comprising contacting the oral surface with a particle according to claim 1.

16. A method for maintaining or promoting the systemic health in a mammal comprising applying the particles according to claim 1 to an oral surface.

17. A method for inhibiting or reducing deposition of biofilm or attachment of microbes to an oral surface comprising contacting the surface with a particle according to claim 1.

18. The oral composition of claim 1 which is a dentifrice composition selected from the group consisting of a toothpaste, gel, powder and a mouth wash.

* * * * *